(12) United States Patent
Fabien

(10) Patent No.: US 11,980,712 B2
(45) Date of Patent: May 14, 2024

(54) DEVICE FOR INHALATION-SYNCHRONIZED DISPENSING OF A FLUID PRODUCT

(71) Applicant: APTAR FRANCE SAS, Le Neubourg (FR)

(72) Inventor: David Fabien, Corseul (FR)

(73) Assignee: APTAR FRANCE SAS, Le Neubourg (FR)

(*) Notice: Subject to any disclaimer, the term of this patent is extended or adjusted under 35 U.S.C. 154(b) by 1060 days.

(21) Appl. No.: 16/757,090

(22) PCT Filed: Oct. 18, 2018

(86) PCT No.: PCT/FR2018/052594
§ 371 (c)(1),
(2) Date: Apr. 17, 2020

(87) PCT Pub. No.: WO2019/077276
PCT Pub. Date: Apr. 25, 2019

(65) Prior Publication Data
US 2020/0246562 A1 Aug. 6, 2020

(30) Foreign Application Priority Data
Oct. 18, 2017 (FR) ........................ 1759800

(51) Int. Cl.
*A61M 15/00* (2006.01)

(52) U.S. Cl.
CPC ...... *A61M 15/0095* (2014.02); *A61M 15/008* (2014.02); *A61M 15/009* (2013.01);
(Continued)

(58) Field of Classification Search
CPC ............ A61M 15/0021; A61M 15/008; A61M 15/009; A61M 15/0095; A61M 2205/276;
(Continued)

(56) References Cited

U.S. PATENT DOCUMENTS 3,456,646 A 7/1969 Phillips et al.
3,789,843 A * 2/1974 Armstrong ........ A61M 15/0091
128/200.23
(Continued)

FOREIGN PATENT DOCUMENTS

NZ 562769 A 12/2010
WO 2004/028608 A1 4/2004
(Continued)

OTHER PUBLICATIONS

International Search Report of PCT/FR2018/052594 dated Feb. 1, 2019 [PCT/ISA/210].
(Continued)

*Primary Examiner* — Timothy A Stanis
(74) *Attorney, Agent, or Firm* — Sughrue Mion, PLLC

(57) ABSTRACT

An inhalation-synchronized fluid dispenser device having a body (10) with a mouthpiece (400), a reservoir (100), a valve (200) assembled by a fastener element (5) on the reservoir (100). The device includes a blocking element (500) that pivots about a pivot axis B between a blocking position and an actuation position; a trigger element (600) that pivots about a pivot axis C; and an inhalation-controlled trigger system. The device includes an actuator member (800) mounted to move axially between a rest position and a primed position. A spring (850) is arranged so that when the actuator member (800) moves towards its primed position, the spring (850) is compressed, so as to transmit an axial force (F) to the reservoir (100).

19 Claims, 7 Drawing Sheets

(52) U.S. Cl.
CPC ... *A61M 15/0021* (2014.02); *A61M 2205/276* (2013.01); *A61M 2205/3331* (2013.01); *A61M 2205/3553* (2013.01); *A61M 2205/3584* (2013.01); *A61M 2205/3592* (2013.01); *A61M 2205/52* (2013.01); *A61M 2205/8206* (2013.01)

(58) Field of Classification Search
CPC .. A61M 2205/3331; A61M 2205/3553; A61M 2205/3584; A61M 2205/3592; A61M 2205/52; A61M 2205/8206
See application file for complete search history.

(56) References Cited

U.S. PATENT DOCUMENTS

| | | | | |
|---|---|---|---|---|
| 5,069,204 | A | * | 12/1991 | Smith ............... A61M 15/0091 128/200.23 |
| 5,119,806 | A | | 6/1992 | Palson et al. |
| 6,397,838 | B1 | * | 6/2002 | Zimlich, Jr. ........ A61M 15/008 128/200.14 |
| 2002/0088458 | A1 | * | 7/2002 | Christrup .......... A61M 15/0068 128/200.14 |
| 2008/0156321 | A1 | | 7/2008 | Bowman et al. |
| 2012/0103329 | A1 | * | 5/2012 | Smith ................. A61M 5/2033 128/203.12 |

FOREIGN PATENT DOCUMENTS

| WO | 2006/115732 A2 | 11/2006 |
|---|---|---|
| WO | 2008/070516 A2 | 6/2008 |
| WO | 2010/003846 A1 | 1/2010 |
| WO | 2013/038169 A1 | 3/2013 |
| WO | 2013/178951 A1 | 12/2013 |
| WO | 2017/176704 A1 | 10/2017 |

OTHER PUBLICATIONS

International Preliminary Report on Patentability with translation of Written Opinion dated Apr. 30, 2020, in International Application No. PCT/FR2018/052594.

* cited by examiner

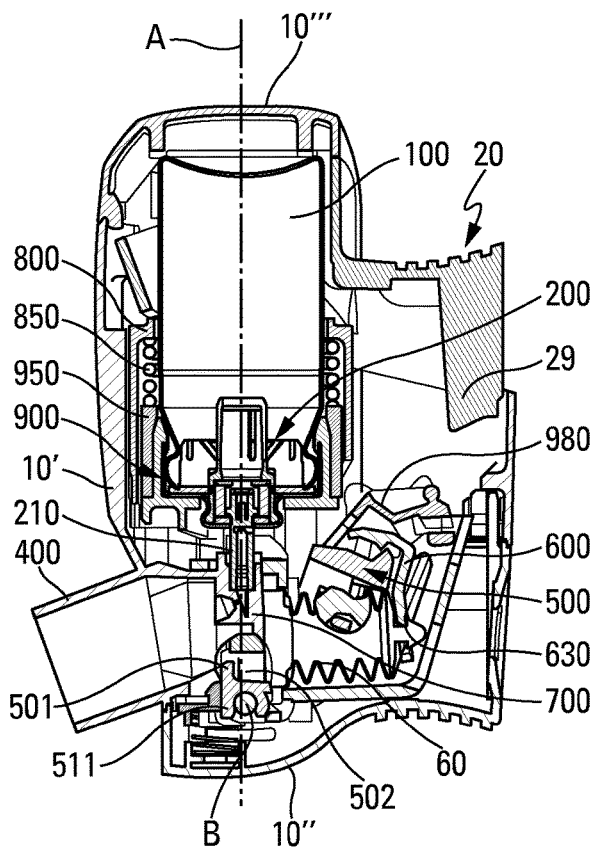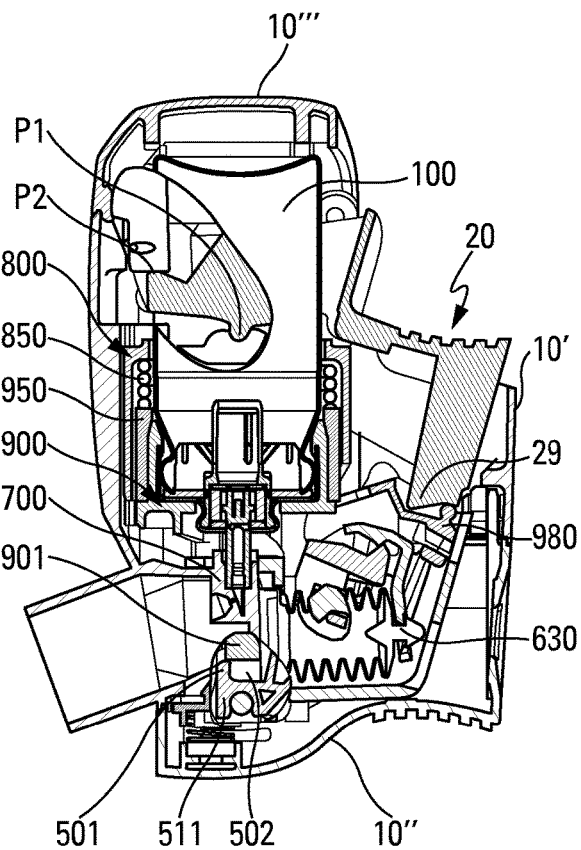
Fig. 6　　　　Fig. 7
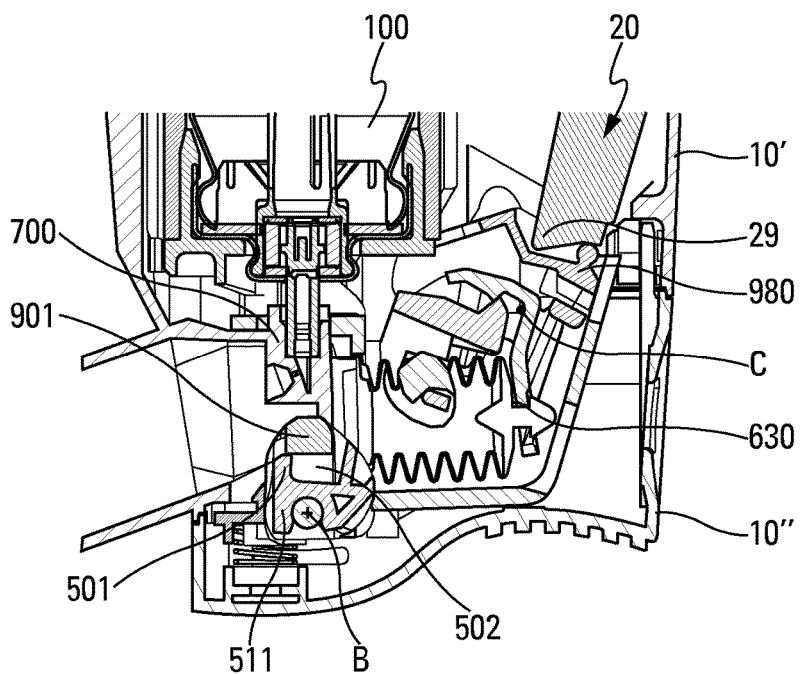
Fig. 8

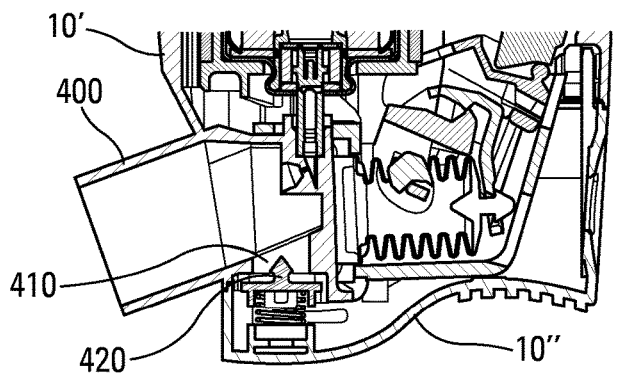
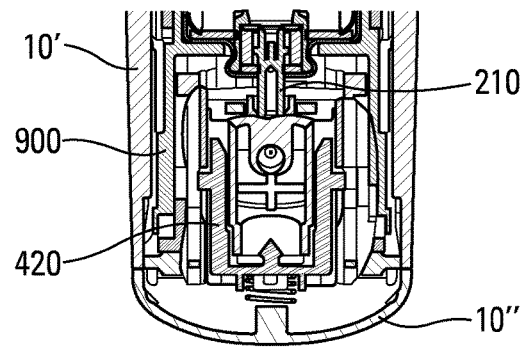
Fig. 18  Fig. 19
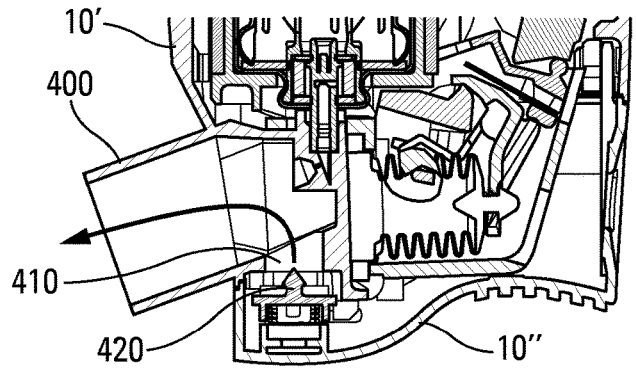
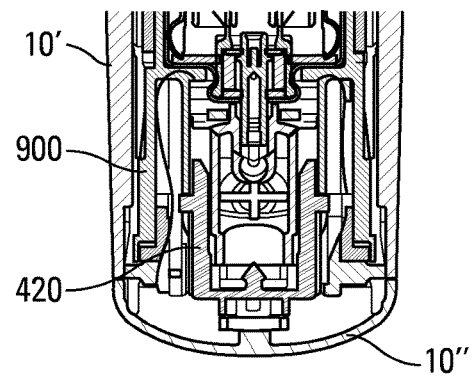
Fig. 20  Fig. 21
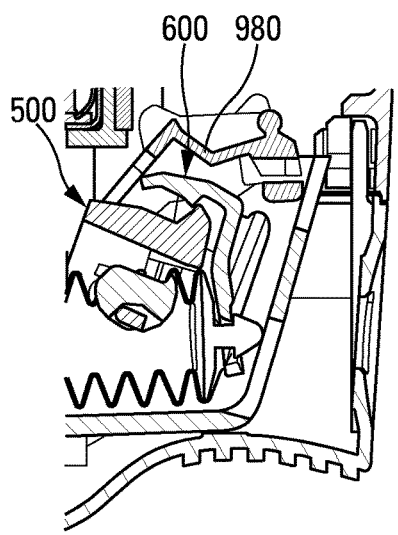
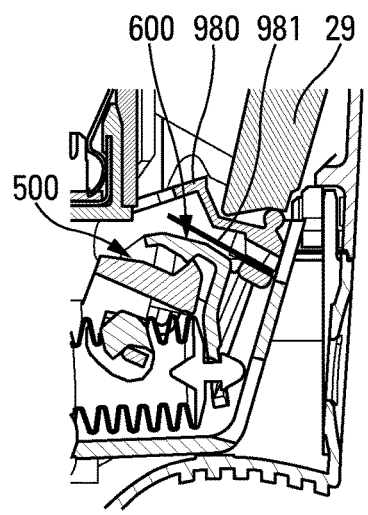
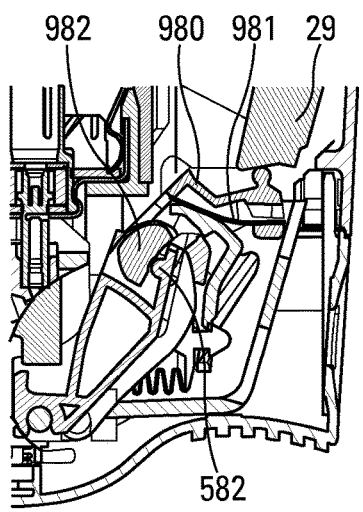
Fig. 22  Fig. 23  Fig. 24

DEVICE FOR INHALATION-SYNCHRONIZED DISPENSING OF A FLUID PRODUCT

CROSS REFERENCE TO RELATED APPLICATIONS

This application is a National Stage of International Application No. PCT/FR2018/052594, filed Oct. 18, 2018, claiming priority to French Patent Application No. 1759800, filed Oct. 18, 2017.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation. Unfortunately, when the latch releases accidentally, the device is actuated automatically and the dose is dispensed, even when the user does not want it.

Documents WO 2004/028608, U.S. Pat. Nos. 3,456,646, 5,119,806, WO 2017/176704, NZ 562 769, US 2008/156321, WO 2008/070516, WO 2010/003846, and WO 2013/178951 describe prior-art devices.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation.

Another object of the present invention is to provide an inhalation-synchronized fluid dispenser device that minimizes the risks of accidental or unwanted actuation.

Another object of the present invention is to provide an inhalation-synchronized fluid dispenser device that does not present an actuation threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

Another object of the present invention is to provide an inhalation-synchronized fluid dispenser device that avoids the risks of the valve malfunctioning as a result of the valve chamber not filling properly after actuation.

The present invention thus provides an inhalation-synchronized fluid dispenser device comprising a body provided with a mouthpiece, a fluid reservoir containing a fluid and a propellant gas being mounted to slide axially relative to said body, a metering valve including a valve member being assembled by means of a fastener element, such as a crimping cap, on said reservoir for selectively dispensing the fluid, said device further comprising:
- a blocking element that pivots about a pivot axis B between a blocking position in which said metering valve cannot be actuated, and an actuation position in which said metering valve can be actuated;
- a trigger element that pivots about a pivot axis C between a locking position in which it blocks said blocking element in its blocking position, and a release position in which it does not block said blocking element; and
- an inhalation-controlled trigger system including an inhalation-sensitive member that is deformable and/or movable under the effect of inhaling, said inhalation-sensitive member co-operating with said trigger element, so that when said inhalation-sensitive member is deformed and/or moved, it moves and/or deforms said trigger element towards its release position, thereby making it possible to move and/or deform said blocking element from its blocking position towards its actuation position;
- said device comprising an actuator member that is mounted to move axially, in particular in sliding, in said body between a rest position and a primed position, a spring being arranged between said actuator member and said reservoir or an element that is secured to said reservoir, so that when said actuator member moves towards its primed position, said spring is compressed, so as to transmit an axial force F to said reservoir, said axial force F extending along an axis Y that is perpendicular to said pivot axis B of said blocking element, said axis Y being spaced apart from said pivot axis B by a distance $\underline{d}$ that is not zero, said distance $\underline{d}$ being less than 2.5 millimeters (mm), advantageously less than 1 mm, preferably about 0.4 mm.

Advantageously, a ring is fastened, in particular snap-fastened, around said fastener element, said ring including an axial projection that co-operates with said blocking element, such that in the blocking position of said blocking element, said axial projection of said ring co-operates with an axial blocking extension of said blocking element, thereby preventing said reservoir from moving axially, and in the actuation position of said blocking element, said axial projection of said ring co-operates with an axial recess of said blocking element, thereby enabling said reservoir to move axially.

Advantageously, in the blocking position of said blocking element, said axial projection of said ring urges said blocking element towards its actuation position.

Advantageously, said hoop is engaged around said ring.

Advantageously, said blocking element includes a locking projection that, in the locking position of the trigger element, co-operates with a locking shoulder of said trigger element so as to define a latch that prevents said blocking element from moving and/or deforming out of its blocking position.

Advantageously, in the blocking position, the force F' exerted by said locking projection of said blocking element on said locking shoulder of said trigger element extends along an axis Z that is perpendicular to said pivot axis C of said trigger element.

Advantageously, said axis Z is spaced apart from said pivot axis C by a distance $\underline{d}'$ that is not zero, said distance $\underline{d}'$ being less than 2 mm, advantageously less than 1 mm, preferably about 0.25 mm.

Advantageously, in the locking position of the trigger element, said latch forms a first contact point between said blocking element and said trigger element, said blocking element including a bearing projection that, in the locking position of the trigger element, co-operates with a bearing surface of said trigger element so as to form, in the locking position of the trigger element, a second contact point between said blocking element and said trigger element, said second contact point being, in the locking position of the trigger element, at a distance from said axis C of the trigger element that is greater than the distance between said axis C and said first contact point.

Advantageously, a laterally-actuated pusher is mounted to move in pivoting and in translation on said body between a rest position and a working position, movement of said laterally-actuated pusher towards its working position moving said actuator member axially towards its primed position.

Advantageously, said laterally-actuated pusher includes a first bearing zone P1 for bearing against said actuator member, and a second bearing zone P2 for bearing against the body.

Advantageously, said first bearing zone P1 is a pivot point, and said second bearing zone P2 is a surface for radial sliding.

Advantageously, said device includes a blocking member that is movable and/or deformable between a blocking position and a non-blocking position, said blocking member, in its blocking position, co-operating with said trigger element so as to prevent it from moving towards its release position, said laterally-actuated pusher including a projection that co-operates with said blocking member when said laterally-actuated pusher is moved towards its working position, so as to move and/or deform said blocking member towards its non-blocking position.

Advantageously, said inhalation-sensitive member includes a deformable membrane that defines a deformable air chamber, said deformable membrane being fastened to said trigger element, said deformable membrane being deformed during inhaling, so that it moves said trigger element from its locking position towards its release position.

Advantageously, said mouthpiece includes an opening that is connected to the inside of the body, said opening being closed at the start of inhaling by a check valve, such that the inhalation flow due to inhaling initially passes mainly to the trigger system.

Advantageously, said check valve is opened when said ring moves axially together with said reservoir.

These and other characteristics and advantages appear more clearly from the following detailed description, given by way of non-limiting example, and with reference to the accompanying drawings, in which:

FIG. 6 is a diagrammatic section view of the FIG. 1 device, shown in its rest position;

FIG. 7 is a view similar to the view in FIG. 6, shown after the actuator pusher has been actuated and before inhalation;

FIG. 8 is a larger-scale diagrammatic view of a detail of FIG. 7;

FIG. 18 is a diagrammatic and fragmentary side view in section of the FIG. 1 device, shown in its rest position;

FIG. 19 is a diagrammatic and fragmentary front view in section of the FIG. 1 device, shown in its rest position;

FIG. 20 is a view similar to the view in FIG. 18, shown after actuation;

FIG. 21 is a view similar to the view in FIG. 4419, shown after actuation; and FIGS. 22 to 24 are diagrammatic and fragmentary section views of the FIG. 1 device, shown respectively in its rest position, during actuation, and during return towards its rest position.

Figure 1:
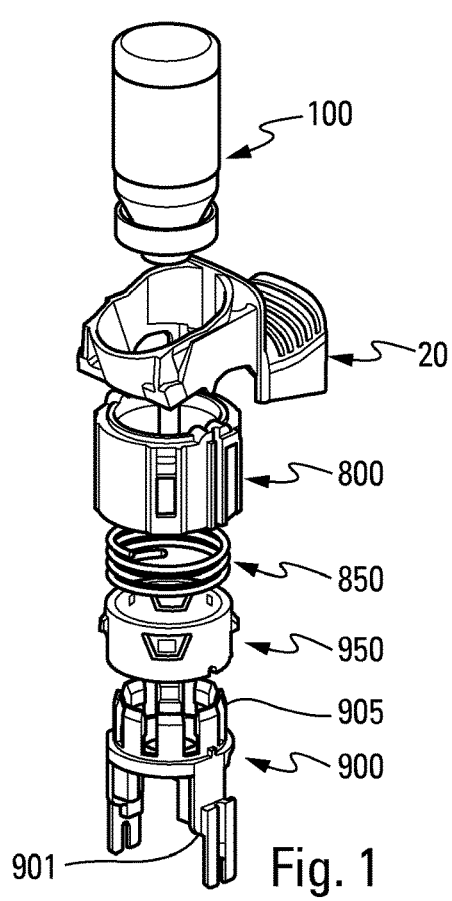
FIG. 1 is an exploded diagrammatic and fragmentary perspective view of a fluid dispenser device, in an advantageous embodiment.
Figure 2:
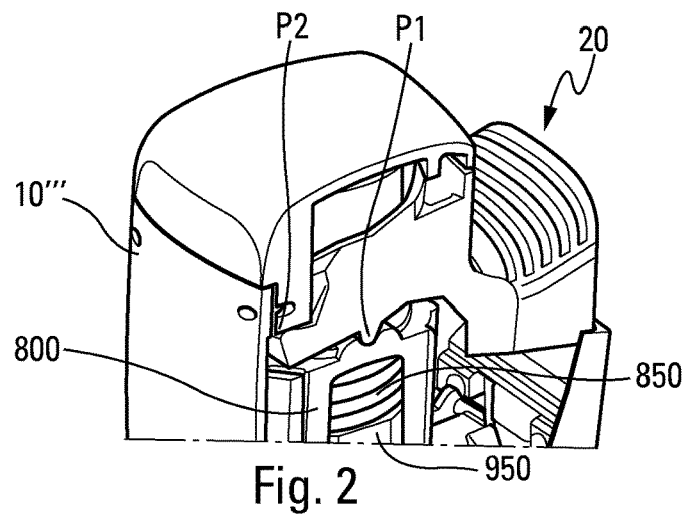
FIG. 2 is a cut-away diagrammatic perspective view of a portion of the FIG. 1 device, shown after assembly and in its rest position.
Figure 3:
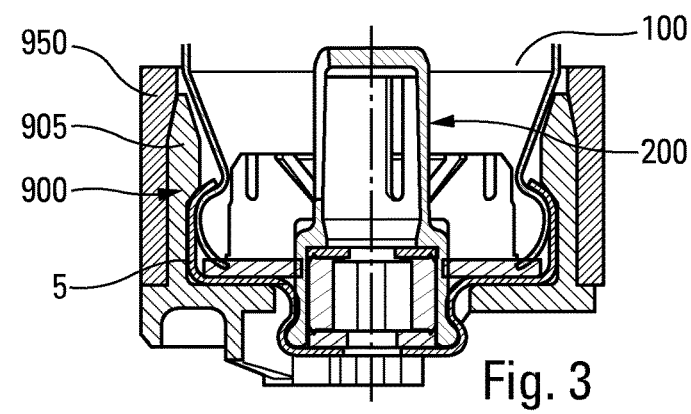
FIG. 3 is a diagrammatic section view of another portion of the FIG. 1 device, shown after assembly and in its rest position.

In the description, the terms "top", "bottom", "upwards", and "downwards" refer to the position of the device as shown in particular in FIGS. 6 to 8 and 12 to 24. The terms "axial" and "radial", except when specified in some other way, are relative to the vertical central axis A of the valve shown in FIG. 6. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show advantageous embodiments of the invention, but naturally one or more of the component parts described below could be made in some other way, while providing functions that are similar or identical.

With reference to the drawings, the device includes a body 10 provided with a mouthpiece 400.

The body 10 may be made as a single piece or out of a plurality of parts that are assembled together. In the non-limiting examples shown, the body 10 comprises three portions, a central portion 10', a bottom portion 10", and a top portion 10'''. In the description below, the body is designated, in overall manner, by the numerical reference 10.

The mouthpiece 400 defines a dispenser orifice through which the user inhales while the device is being used. The mouthpiece 400 may be made integrally with the body 10. In the embodiments shown in the drawings, it is formed on the bottom body portion 10". A removable protective cap (not shown) may be provided on said mouthpiece 400, in particular while it is being stored, that the user removes before use.

The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body, and a valve member 210 that, during actuation, is axially movable relative to said valve body, and thus relative to said reservoir 100. The metering valve 200 can be of any appropriate type. It is fastened to the reservoir 100 via a fastener element 5, preferably a crimped cap, preferably with a neck gasket interposed therebetween.

Advantageously, during actuation, the valve member 210 is stationary relative to the body 10, and it is the reservoir 100 that is moved axially relative to the body 10 between a distal position, which is the rest position, and a proximal position, which is the actuation position.

The outlet orifice of the valve member 210 of said metering valve 200 is connected via a channel to said mouthpiece 400 through which the user inhales the fluid to be dispensed. In known manner, said valve member 210 is received in a valve well 700 that defines said channel, at least in part.

The device includes a ring 900 that is advantageously fastened around said fastener element 5, e.g. by snap-fastening by means of snap-fastener tabs 905. Advantageously, a hoop 950 is engaged around said ring 900, so as to hold said snap-fastener tabs 905 in their snap-fastened position. The ring 900 includes an axial projection 901 having a function that is described below.

An actuator member 800 is advantageously assembled around the reservoir 100. The actuator member 800 includes a hollow sleeve 801 that is arranged in the body 10 around the reservoir 100, with a spring 850 arranged between the bottom of said hollow sleeve 801 and the reservoir 100 or an element that is secured to said reservoir 100, such as the ring 900 or the hoop 950. The hollow sleeve 801 is axially movable, in particular in sliding, relative to said reservoir 100 between a rest position and a primed position. Thus, when the user wishes to actuate the metering valve 200, the user presses on said actuator member 800. This moves said hollow sleeve 801 axially towards its primed position and thus compresses said spring 850, which thus transmits an axial force F to said reservoir 100, in particular via said hoop 950, in the embodiment shown. The axial force F is substantially the same on each actuation. While the user continues to press on said actuator member 800, said spring 850 is compressed and drives said reservoir 100 axially towards its actuated position.

A laterally-actuated pusher 20 is advantageously mounted to move in pivoting and in translation on the body 10. When moved from its rest position shown in particular in FIG. 6, to its working position shown in particular in FIG. 7, the pusher 20 moves said actuator member 800 axially so as to compress the spring 850.

The laterally-actuated pusher 20 advantageously includes a first bearing zone P1 for bearing against said actuator member 800, and a second bearing zone P2 for bearing against the body 10.

In the embodiment shown in the figures, the first bearing zone P1 is a pivot point, and the second bearing zone P2 is a surface for radial sliding. While the pusher 20 is being actuated, the pivot point P1 slides axially downwards relative to the body 10, while the contact point in the zone P2 moves radially inwards relative to the body 10.

Figure 4:
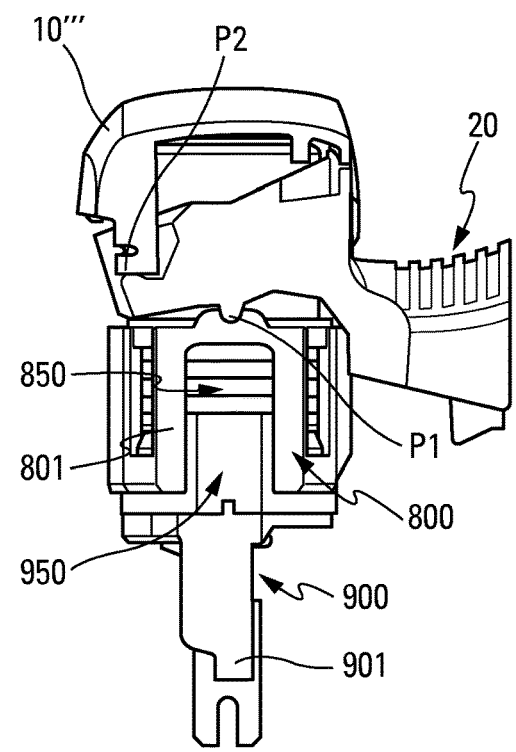
FIG. 4 is a cut-away diagrammatic perspective view of the FIG. 1 device, shown after assembly and in its rest position.
Figure 5:
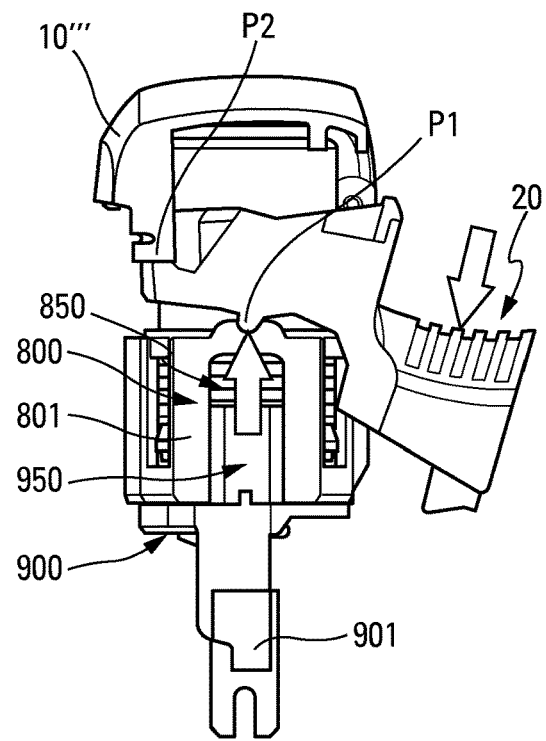
FIG. 5 is a view similar to the view in FIG. 4, shown after the actuator pusher has been actuated.
Figure 9:
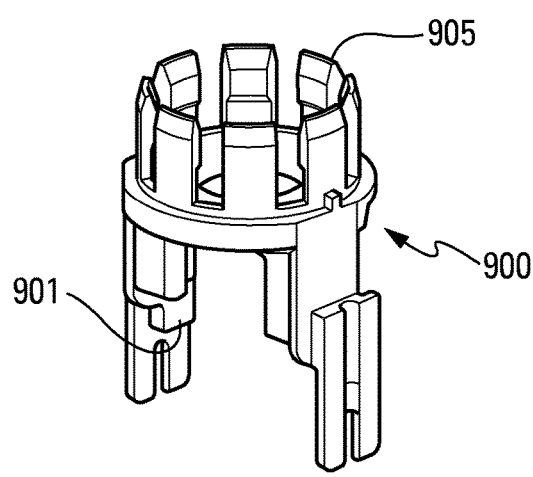
FIG. 9 is a diagrammatic perspective view of the ring.

In this embodiment, the pusher 20 is thus movable both in pivoting and in translation. This makes it possible to reduce the force required from the user, while remaining compact. This reduction makes it possible to actuate the valve 200 with a force that is smaller than the force that would be required if the user had to press axially on the bottom of the reservoir 100. In particular, in the embodiment shown, and as can be seen clearly in FIGS. 4 and 5, the force required to actuate the valve 200 axially is typically in the range 40 newtons (N) to 45 N (depending on the stiffness of the spring 850), while the force required to actuate the laterally-actuated pusher 20 is only about 15 N. In this embodiment, the reduction is thus about a factor of three. It is possible to increase this ratio further, in particular by acting on the shapes of the various parts.

While the user continues to press on said pusher, said spring 850 is compressed and drives said reservoir 100 axially towards its actuated position.

After each actuation, when the user releases the pressure on the pusher 20, which occurs naturally, said pusher returns automatically towards its rest position under the effect of the spring 850. After the metering valve 200 has been actuated, this makes it possible to avoid the risk of said metering valve remaining in its actuated position, which could cause the valve chamber to fill with air and the following dose to be incomplete, or it could cause the valve to leak. This is one of the problems that currently exist with devices that are currently on the market.

The device includes a blocking element 500 that is movable and/or deformable between a blocking position in which said metering valve 200 cannot be actuated, and an actuation position in which said metering valve 200 can be actuated. In the rest position, said blocking element 500 is in the blocking position, and it is the user inhaling through the mouthpiece 400 that moves and/or deforms said blocking element 500 towards its actuation position. In other words, so long as the user does not inhale, it is impossible to actuate the metering valve 200, and it is only when the user inhales that said metering valve 200 can be actuated, by moving the reservoir 100 axially in the body 10.

As described in greater detail below, the blocking element 500, in its blocking position, prevents the reservoir 100 from moving axially in the body 10. During inhaling, the blocking element 500 is moved and/or deformed so that it no longer prevents the reservoir 100 from moving axially in the body 10. Thus, after inhaling, such axial movement of the reservoir 100 causes the metering valve 200 to be actuated and a dose of fluid to be dispensed, synchronously with the inhaling.

Thus, in the absence of inhaling, there is no risk of an active dose of fluid being lost by accidental or incomplete actuation during which the user does not inhale. Actuating the valve 200 and expelling a dose of fluid are thus possible only when the user inhales and simultaneously actuates the actuator pusher 20. In a variant, it is also possible to envisage that the user presses axially, directly on the bottom of the reservoir, or it is possible to use an automatic actuator system that would apply the axial pressure on the reservoir independently of the user.

The device includes a trigger system that is controlled by the user inhaling, and that is for moving and/or deforming said blocking element 500 from its blocking position towards its actuation position, when the user inhales through the mouthpiece 400.

The trigger system includes an inhalation-sensitive member 60 that is deformable and/or movable under the effect of inhaling, the inhalation-sensitive member 60 being adapted, when it is deformed and/or moved, to make it possible to move and/or deform said blocking element 500 from its blocking position towards its actuation position.

As described in greater detail below, the inhalation-sensitive member may be made in the form of a deformable air chamber 60, e.g. a bellows or a deformable pouch.

In this way, the inhalation-controlled trigger system is not situated in the user's suction flow but is formed by a specific chamber, namely the air chamber 60. This differs from systems that operate by means of a flap that moves/deforms in the suction flow, in which systems, after triggering, the user sucks in the air that exists on each side of the flap. In this embodiment, the system operates under suction and the user sucks in only the small volume of air that was inside the air chamber 60 before it deformed. In the invention, the system is thus much more stable and effective.

The blocking element 500 is advantageously mounted to pivot about an axis B on the body 10, between a blocking position and an actuation position. In the embodiment shown, said axis B may be formed by projections that are provided on a bottom surface of the body 10, the blocking element 500 including complementary profiles 511 that are adapted to pivot on said projections. Other embodiments are also possible.

Figure 11:
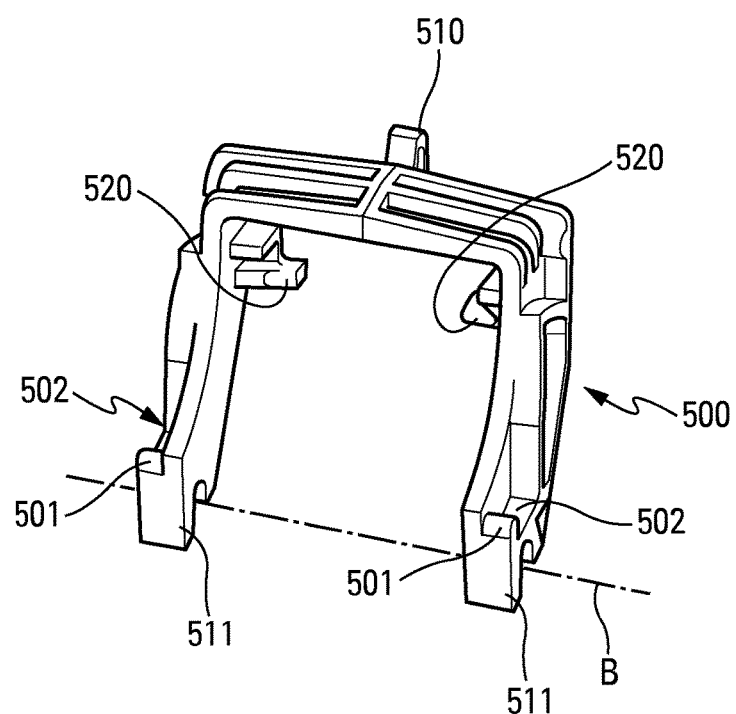
FIG. 11 is a diagrammatic perspective view of the blocking element.
Figure 12:
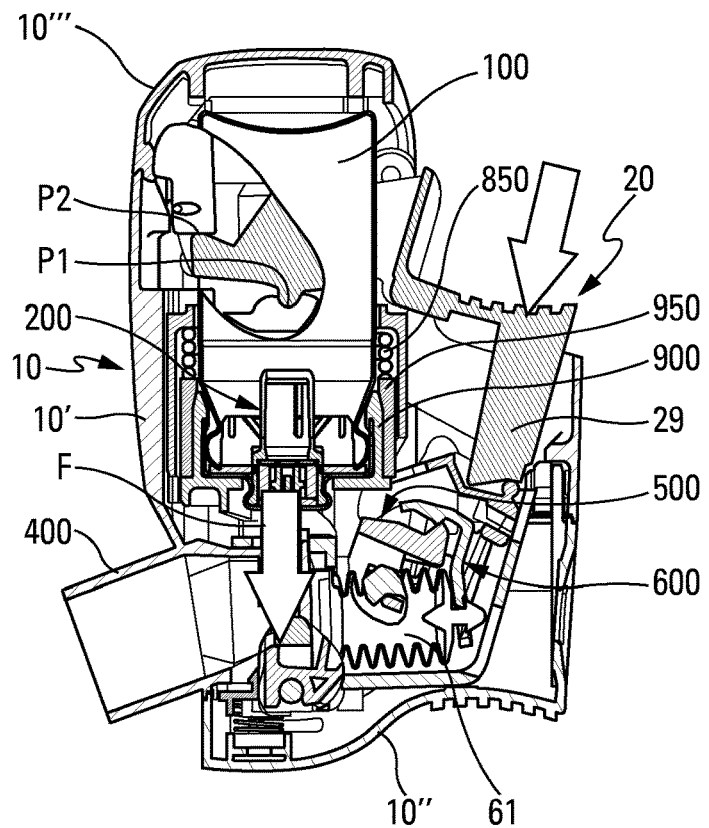
FIG. 12 is a view similar to the view in FIG. 7, shown at the start of inhalation.

The blocking element 500 includes at least one, preferably two, blocking extensions 501, each of which co-operates in the blocking position with a respective axial projection 901 of said ring 900 that is secured to the reservoir 100. FIG. 11 is a perspective view of the blocking element 500.

When the blocking element 500 moves towards its actuation position, in particular by pivoting about the axis B, each blocking extension 501 moves out of contact with its respective axial projection 901. In particular, adjacent to each blocking extension 501, said blocking element 500 includes an axial recess 502 in which the respective axial projection 901 can slide axially, thereby enabling said reservoir 100 to slide axially in said body 10, causing the valve 200 to be actuated and a dose of fluid to be dispensed.

Figure 10:
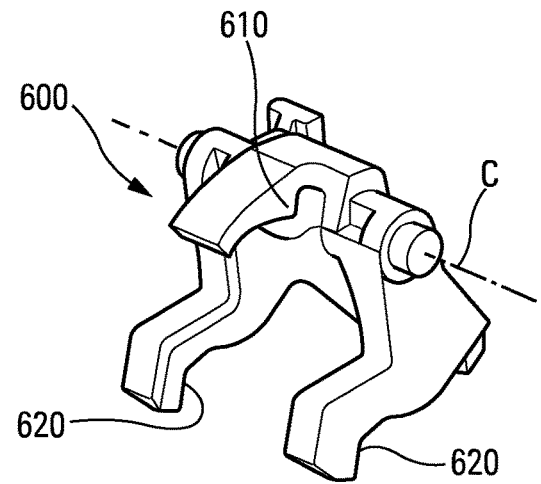
FIG. 10 is a diagrammatic perspective view of the trigger element.

The blocking element 500 is held in its blocking position by a trigger element 600. FIG. 10 is a perspective view of the trigger element 600. The trigger element 600 is advantageously mounted to pivot about an axis C on the body 10, between a locking position in which it blocks said blocking element 500 in its blocking position, and a release position in which it no longer blocks said blocking element 500.

Advantageously, the axes B and C are parallel.

The blocking element 500 and the trigger element 600 co-operate with each other to define a latch. In particular, said trigger element 600 includes a locking shoulder 610 that, in the locking position, co-operates with a locking projection 510 of the blocking element 500, preventing said blocking element 500 from pivoting out of its blocking position. Thus, when said trigger element 600 is in its locking position, it prevents the blocking element 500 from moving towards its actuation position, thereby preventing the reservoir 100 from moving axially and the metering valve 200 from thus being actuated.

The blocking system of the present invention thus includes two stages: a first stage formed by the latch between the blocking element 500 and the trigger element 600, and a second stage formed by the blocking between the blocking element 500 and the reservoir 100, via the ring 900.

The blocking system makes it possible to unlock a large force (typically about 40 N to 45 N) by means of a small force generated by inhaling. The blocking element 500 stops the reservoir 100 from moving in translation when it is subjected to a force F (e.g. of 45 N) by means of the user pressing on the actuator member 800, preferably via the actuator pusher 20. The blocking element 500 interacts with the trigger element 600, and it is both blocked and released by said trigger element. The movement of said trigger element 600 is controlled by inhaling.

The shape of the blocking system enables very large amplification (locked force/unlocked force), typically of about 100.

The blocking element 500 and the trigger element 600 preferably have two contact points that are spaced apart:

a first contact point, formed by the latch defined between the locking shoulder 610 and the projection 510, is advantageously situated close to the pivot axis C of the trigger element 600; and a second contact point at a distance from the first contact point, formed by the co-operation between a lateral projection 520 of the blocking element 500 and a bearing surface 620 of the trigger element 600; advantageously, in the locking position, the second contact point is at a distance from the axis C of the trigger element 600 that is greater than the distance between said axis C and the first contact point; advantageously, the second contact point is the first contact that is broken while actuating the device, when the user begins to inhale.

Figure 13:
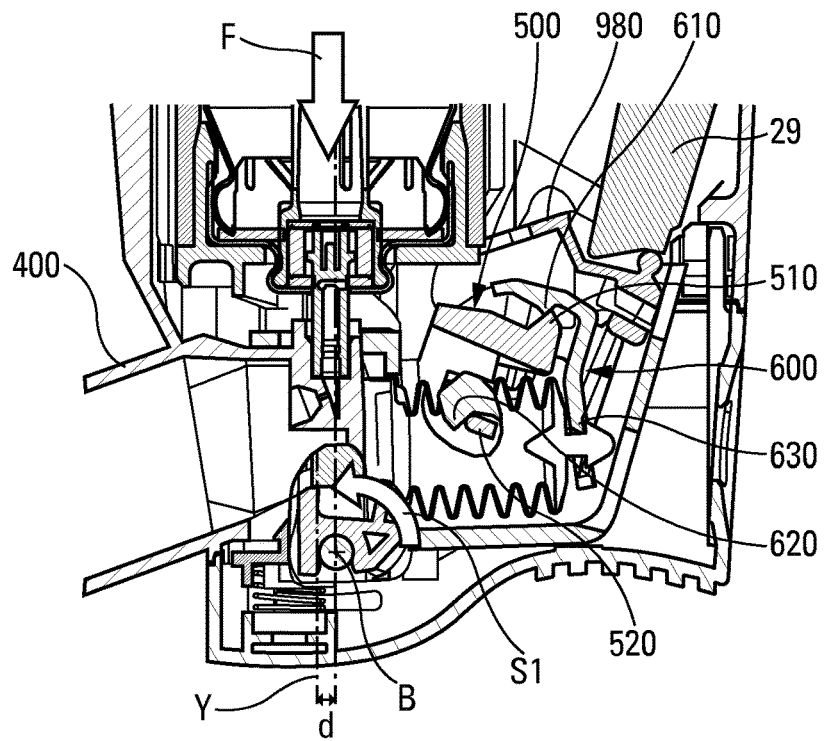
FIG. 13 is a larger-scale diagrammatic view of a detail of FIG. 12.
Figure 14:
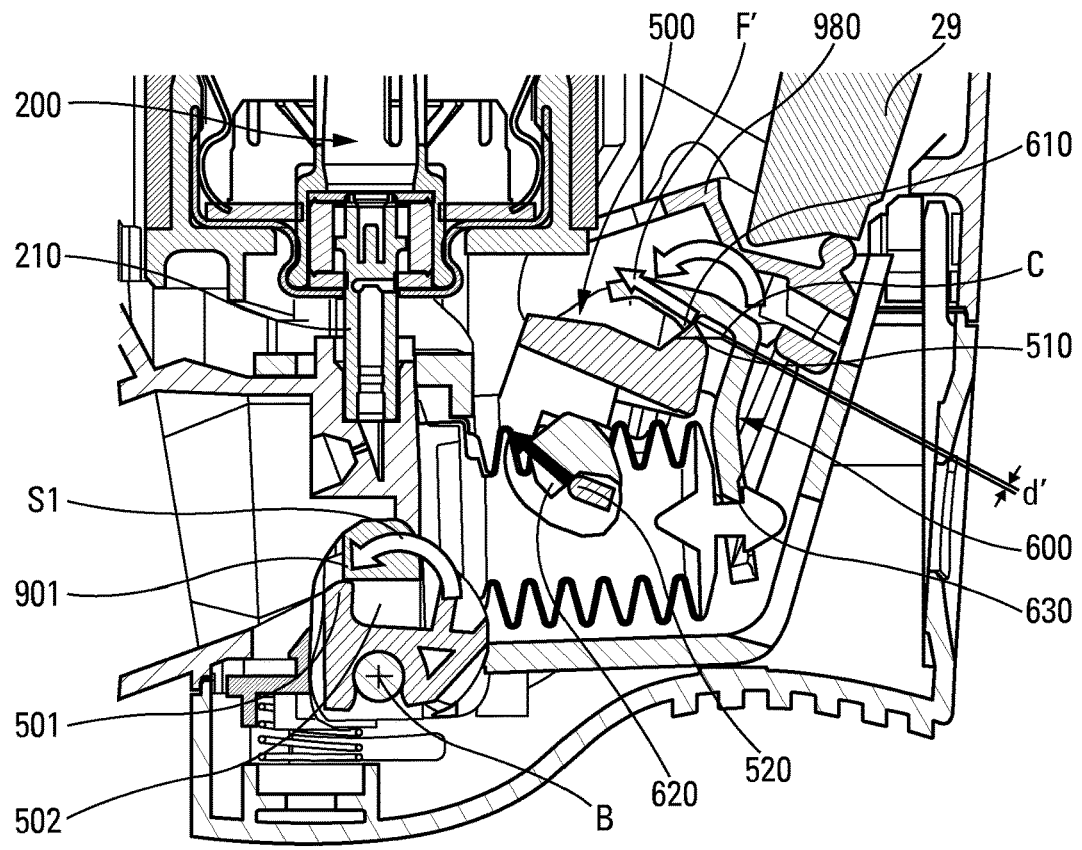
FIGS. 14 to 17 are views similar to the view in FIG. 13, shown at various stages of an actuation cycle.

In the blocking position, the force F generated by the actuator member 800 pressing axially on the hoop 950 that is secured to the reservoir 100 is applied, via the axial projections 901 of the ring 900, to the blocking element 500 at the extensions 501, causing said blocking element to pivot in a direction S1 that reinforces the closed position of the latch and makes it stable. In particular, FIGS. 13 and 14 show this blocking position.

Figure 15:
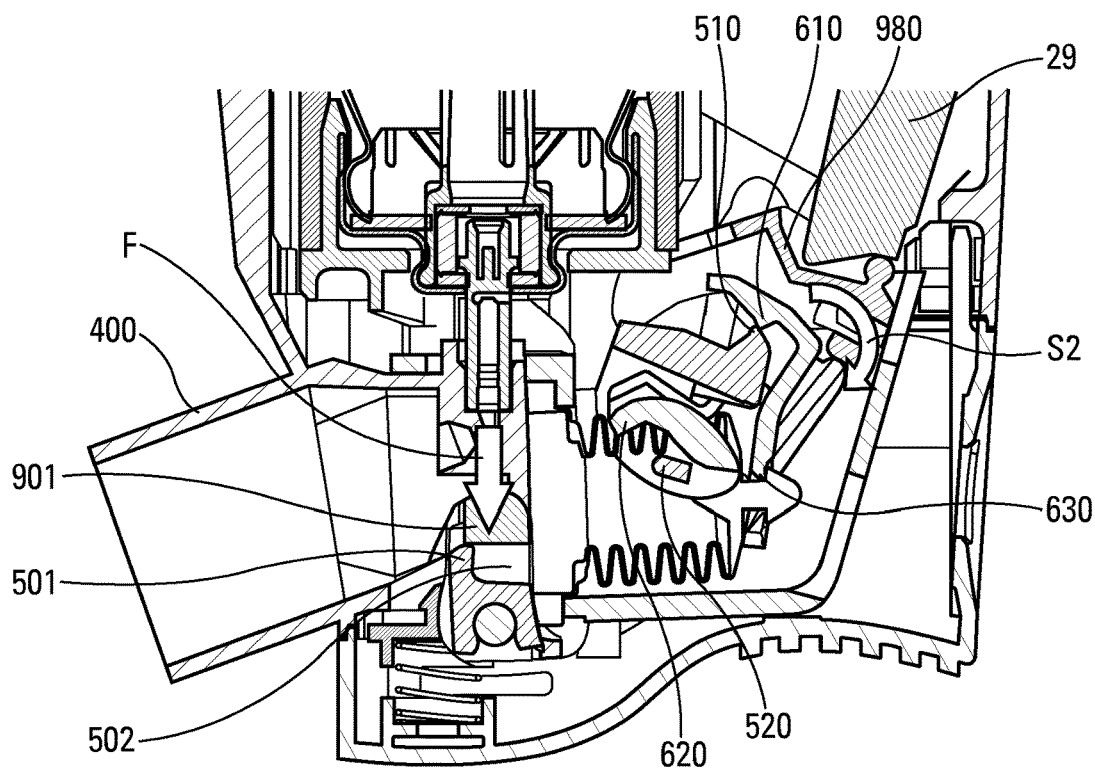
Figure 16:
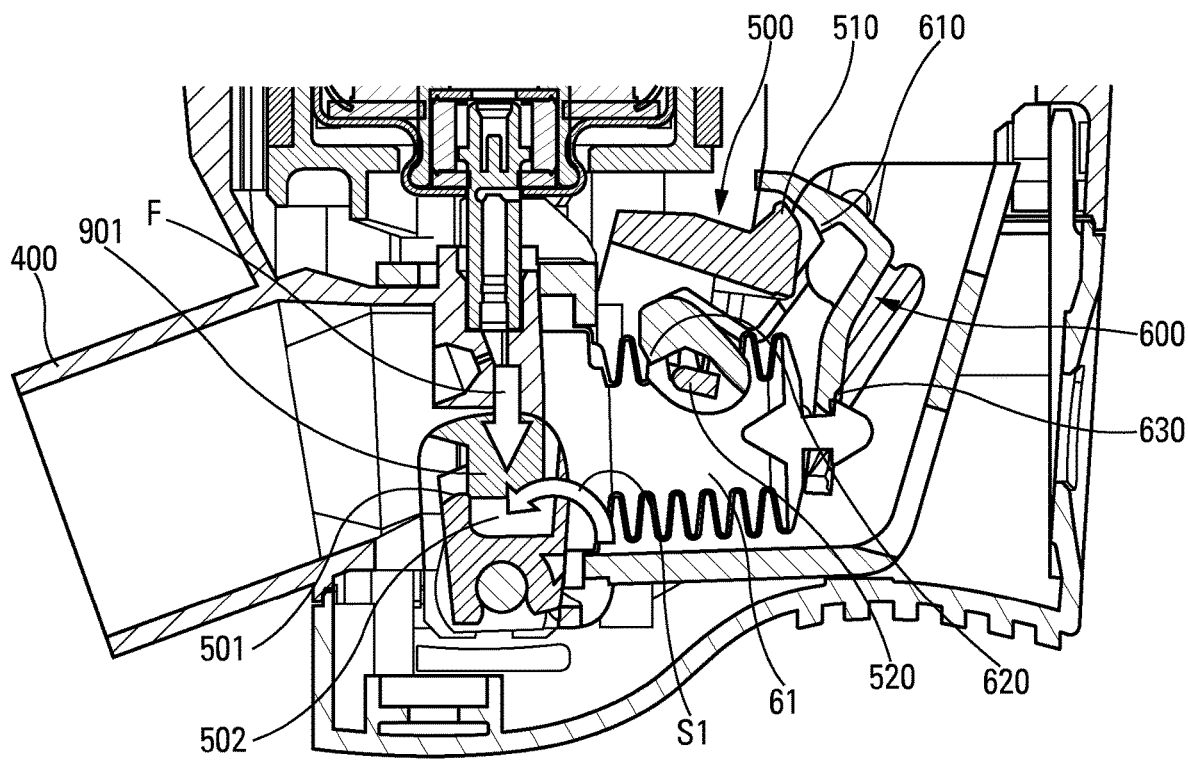

The unlocking force generated by inhaling is applied to the trigger element 600 by the deformable membrane 61, preferably at a point 630 at a distance from the pivot axis C; the unlocking force seeks to pivot said trigger element 600 in the direction S2 opposite to the direction S1, as shown in FIG. 15.

The torque to which the blocking element 500 is subjected is controlled by the distance between the axis along which the force F is applied to the blocking extensions 501 of the blocking element, and the pivot axis B of said blocking element 500. It is desirable for the distance $\underline{d}$ to be as small as possible, in order for the torque to be as small as possible. The distance $\underline{d}$, shown in FIG. 13, is not zero, and is less than 2 mm, advantageously less than 1 mm, preferably about 0.4 mm.

The torque to which the trigger element 600 is subjected is controlled by the distance between the axis conveying the force F' to which the trigger element 600 is subjected by the blocking element 500, and the pivot axis C of said trigger element 600. Once again, it is desirable for the distance $\underline{d}'$ to be as small as possible, in order for the torque to be as small as possible. The distance $\underline{d}'$, shown in FIG. 14, is not zero, and is less than 2 mm, advantageously less than 1 mm, preferably about 0.25 mm.

By means of this latch force system, the force necessary to cause the trigger element 600 to pivot is very small and may be generated by the deformable membrane 61, that makes it possible to transform the suction generated by inhaling into unlocking force.

Advantageously, the mouthpiece 400 includes an opening 410 that is connected to the inside of the body 10. The opening 410 is closed at rest and at the start of inhaling by a check valve 420, so that the inhalation flow due to inhaling initially passes mainly to the trigger system, in this embodiment the deformable air chamber 60. This makes it possible to optimize such triggering by inhaling. When the blocking element 500 moves towards its actuation position under the effect of inhaling, and thus the reservoir 100 moves axially relative to the body 10 so as to actuate the metering valve 200 in order to dispense a dose of fluid, said ring 900, that is secured to the reservoir 100, moves said check valve 420 towards its open position. When said openings 410 are thus opened, during actuation, air is drawn in, thereby making it possible to increase the inhalation flow. This optimizes synchronization between the user inhaling and dispensing the dose, and also promotes good dispensing of the dose into the user's lungs.

Advantageously, the trigger element 600 may be accessible from the outside of the body 10 and/or of the bottom body portion 10'. This makes it possible, if necessary, to move the trigger element 600 manually, so as to be able to actuate the metering valve 200 even without inhaling, e.g. when the person that needs to receive the dose of fluid is incapable of inhaling sufficiently. This is thus a safety measure.

In the embodiments shown in the figures, the inhalation-sensitive member 60 is made in the form of a deformable air chamber. Advantageously, the air chamber comprises a deformable membrane 61 that is connected firstly to said bottom body portion 10' and secondly to said trigger element 600. Advantageously, as can be seen in the figures, the membrane 61 is in the form of a bellows and forms a substantially airtight chamber. Other forms are possible, in particular a mere pouch or diaphragm. A lug may fasten said membrane 61 to an orifice or edge 630 of said trigger element 600.

During inhaling, the deformable membrane 61 deforms and/or contracts under the effect of the suction generated by inhaling, causing the trigger element 600 to move from its locking position towards its release position. This makes it possible to open the latch defined between the blocking element 500 and the trigger element 600, and thus to move said blocking element 500 from its blocking position towards its actuation position.

The valve 200 is thus actuated only at the moment of inhaling, such that the dose of fluid is expelled out of the dispenser orifice simultaneously with inhaling.

Advantageously, the device includes a blocking member 980 that is movable and/or deformable between a blocking position and a non-blocking position. In its blocking position, the blocking member 980 co-operates with the trigger element 600 so as to prevent it from moving towards its release position. The laterally-actuated pusher 20 advantageously includes a projection 29 that co-operates with said blocking member 980 when said laterally-actuated pusher 20 is moved towards its working position. This moves and/or deforms said blocking member 980 towards its non-blocking position.

Thus, when the user inhales without having pressed axially on the reservoir 100, the latch is not unblocked, since the trigger element 600 cannot pivot. Since the air chamber 60 is substantially airtight, and the check valve 420 is closed in the opening 410, the user very quickly realizes that it is not possible to inhale correctly through the mouthpiece, which reminds the user that it is necessary to actuate the pusher first before inhaling. When the user presses on the pusher 20, the blocking member 980 is moved into its non-blocking position. Inhaling thus causes the trigger element 600 to pivot, and thus causes the device to be actuated, as explained above.

Advantageously, the blocking member 980 includes a resilient element (not shown), such as a torsion spring, that resiliently urges said blocking member 980 towards its blocking position, so that when the user releases the actuator pusher 20, said blocking member 980 returns automatically into its blocking position.

Advantageously, this also returns the trigger element 600 into its locking position, e.g. via an appropriate flexible blade 981.

The blocking member 980 also advantageously includes a re-cocking extension 982 that co-operates with a re-cocking portion 582 of the blocking element 500, so that when the blocking member 980 returns into its blocking position, it returns the blocking element 500 into its blocking position.

When the user wishes to use the device, the user places the mouthpiece 400 in the mouth, and exerts axial pressure manually on the actuator pusher 20. The reservoir 100 is blocked and prevented from sliding axially in the body 10 by the blocking extensions 501 of the blocking element 500 that block the axial projections 901 of the ring 900 axially. In parallel, the trigger element 600 is no longer blocked as a result of the movement of the blocking member 980, as can be seen in particular in FIGS. 6 and 7.

Figure 17:
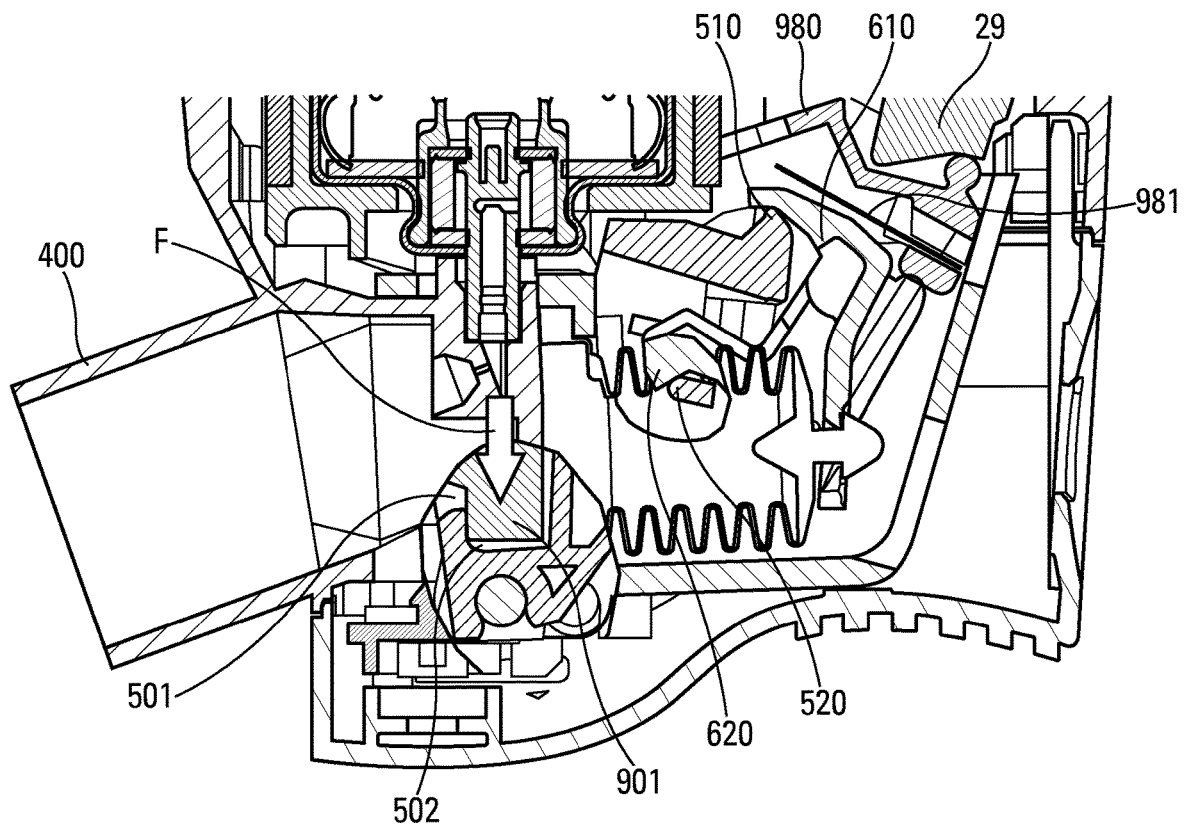

When the user inhales through the mouthpiece 400, the deformable membrane 61 deforms, and this causes the trigger element 600 that is fastened to said deformable membrane 61 to pivot. The movement of the trigger element 600 releases the latch formed between the locking shoulder 610 of the trigger element 600 and the projection 510 of the blocking element 500, as can be seen in FIGS. 14 to 17. Under the effect of the axial force F transmitted by the reservoir 100, the blocking element 500 pivots enabling the reservoir 100 to slide axially in the body 10 towards its dispensing position, and the valve 200 thus to be actuated. In parallel, the ring 900 opens the check valve 20. This dispensing position is shown in FIGS. 17, 20, and 21.

At the end of inhaling, when the user releases the pressure on the bottom of the reservoir 100, in particular by releasing the pressure on the pusher 20, said reservoir 100 rises axially in the body 10 towards its rest position under the effect of the return spring of the valve 200, and the valve member 210 of the metering valve simultaneously returns to its rest position, once again filling the valve chamber with a new dose of fluid. The trigger element 600 is returned into its initial position, in particular by the springiness of the membrane 61 and/or the spring blade 981 of the blocking member 980. The blocking element 500 returns into its blocking position, via the re-cocking extension 982 of the blocking member 980.

The device is thus ready for another utilization.

It should be observed that the device could include an electronic dose counter, advantageously assembled in the body or in the pusher. In particular, the counter could detect the movements of the reservoir. In a variant, the counter could be connected to a sensor, in particular a membrane sensor, that detects the dose of fluid being dispensed, e.g. in the valve well. Such an electronic counter could be actuated in other ways, e.g. by detecting the movement of the valve member of the metering valve relative to the valve body.

The device could thus also include signal-transmitter means for communicating, in particular communicating remotely, information relating to the actuations of the device. In particular, the body and/or the pusher could include a signal-transmitter module, for communicating remotely with any base. Appropriate power supply means could advantageously be provided.

In particular, the electronic module could advantageously comprise a card that includes an electrical switch that sends a pulse. The module could also comprise a display and/or use a Bluetooth or Wifi connection for sending information to an accompanying peripheral. Appropriate sensors, such as flowrate and/or pressure sensors, could be provided for detecting various parameters of the inhalation flow.

The switch could be actuated by means of the movement of the blocking element.

Associated with a dose counter that counts each dose that is actually dispensed, and with the inhalation-synchronized device of the invention, the signal-transmitter means make it possible for each dose that has been dispensed to be transmitted in completely reliable manner, e.g. to a doctor or to any other person wishing to monitor the use of the inhaler device by the user. The inhalation-synchronized device guarantees that the user inhales each time the user actuates the device, and the counter records each dose that is dispensed, together with various associated parameters, such as a timestamp for each dispensing. In this way, the doctor can know very accurately the conditions of use of the device by the user.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to advantageous embodiments and variants, but naturally any modification could be applied thereto by a person skilled in the art, without going beyond the ambit of the present invention, as defined by the accompanying claims.

The invention claimed is:

1. An inhalation-synchronized fluid dispenser device comprising a body provided with a mouthpiece), a fluid reservoir containing a fluid and a propellant gas being mounted to slide axially relative to said body, a metering valve including a valve member being assembled by means of a fastener element on said reservoir for selectively dispensing the fluid, said device further comprising:
   a blocking element that pivots about a pivot axis B between a blocking position in which said metering valve cannot be actuated, and an actuation position in which said metering valve can be actuated;
   a trigger element that pivots about a pivot axis C between a locking position in which it blocks said blocking element in its blocking position, and a release position in which it does not block said blocking element; and
   an inhalation-controlled trigger system including an inhalation-sensitive member that is deformable and/or movable under the effect of inhaling, said inhalation-sensitive member configured to cooperate with said trigger element, so that when said inhalation-sensitive member is deformed and/or moved, said inhalation sensitive member moves and/or deforms said trigger element towards its release position, thereby making it possible to move and/or deform said blocking element from the blocking position towards the actuation position;
   said device comprising an actuator member that is mounted to move axially in said body between a rest position and a primed position, a spring being arranged between said actuator member and said reservoir or an element that is secured to said reservoir, so that when said actuator member moves towards its the primed position, said spring is compressed, so as to transmit an axial force (F) to said reservoir, said axial force (F) extending along an axis Y that is perpendicular to said pivot axis B of said blocking element, said axis Y being spaced apart from said pivot axis B by a distance $\underline{d}$ that is not zero, said distance $\underline{d}$ being less than 2.5 millimeter.

2. A device according to claim 1, wherein a ring is fastened, around said fastener element, said ring including an axial projection that is configured to cooperate with said blocking element, such that in the blocking position of said blocking element, said axial projection of said ring co-operates with an axial blocking extension of said blocking element, thereby preventing said reservoir from moving axially, and in the actuation position of said blocking element, said axial projection of said ring co-operates with an axial recess of said blocking element, thereby enabling said reservoir to move axially.

3. A device according to claim 2, wherein, in the blocking position of said blocking element, said axial projection of said ring urges said blocking element towards its the actuation position.

4. A device according to claim 2, wherein a hoop (950) is engaged around said ring (900).

5. A device according to claim 1, wherein said distance $\underline{d'}$ is less than about 0.25 millimeter.

6. A device according to claim 1, wherein said blocking element includes a locking projection that, in the locking position of the trigger element, is configured to cooperate with a locking shoulder of said trigger element so as to define a latch that prevents said blocking element from moving and/or deforming out of the blocking position.

7. A device according to claim 6, wherein in the blocking position, the force exerted by said locking projection of said blocking element on said locking shoulder of said trigger element extends along an axis Z that is perpendicular to said pivot axis C of said trigger element.

8. A device according to claim 7, wherein said axis Z is spaced apart from said pivot axis C by a distance $\underline{d'}$ that is not zero, said distance $\underline{d'}$ being less than 2 millimeter.

9. A device according to claim 8, wherein said distance $\underline{d'}$ is less than 1 millimeter.

10. A device according to claim 1, wherein in the locking position of the trigger element, said latch forms a first contact point between said blocking element and said trigger element, said blocking element including a bearing projection that, in the locking position of the trigger element, is configured to cooperate with a bearing surface of said trigger element so as to form, in the locking position of the trigger element, a second contact point between said blocking element and said trigger element, said second contact point being, in the locking position of the trigger element, at a distance from said axis C of the trigger element that is greater than the distance between said axis C and said first contact point.

11. A device according to claim 1, wherein a laterally-actuated pusher is mounted to move in pivoting and in translation on said body between a rest position and a working position, movement of said laterally-actuated pusher towards the working position moving said actuator member axially towards the primed position.

12. A device according to claim 11, wherein said laterally-actuated pusher includes a first bearing zone (P1) for bearing against said actuator member, and a second bearing zone (P2) for bearing against the body.

13. A device according to claim 12, wherein said first bearing zone (P1) is a pivot point, and said second bearing zone (P2) is a surface for radial sliding.

14. A device according to claim 11, including a blocking member that is movable and/or deformable between a blocking position and a non-blocking position, said blocking member, in the blocking position, is configured to cooperate with said trigger element so as to prevent said trigger element from moving towards a release position, said laterally-actuated pusher including a projection that co-operates with said blocking member when said laterally-actuated pusher is moved towards the working position, so as to move and/or deform said blocking member towards the non-blocking position.

15. A device according to claim 1, wherein said inhalation-sensitive member includes a deformable membrane that defines a deformable air chamber, said deformable membrane being fastened to said trigger element, said deformable membrane configured to be deformed during inhaling to move said trigger element from the locking position towards the release position.

16. A device according to claim 1, wherein said mouthpiece includes an opening that is connected to the inside of the body, said opening being closed at the start of inhaling by a check valve, such that the inhalation flow due to inhaling initially passes mainly to the trigger system.

17. A device according to claim 16, wherein said check valve is opened when said ring moves axially together with said reservoir.

18. A device according to claim 1, wherein said distance $\underline{d}$ is less than 1 millimeter.

19. A device according to claim 1, wherein said distance $\underline{d}$ is less than about 0.4 millimeter.

* * * * *